(12) United States Patent
Antons et al.

(10) Patent No.: US 6,376,414 B1
(45) Date of Patent: Apr. 23, 2002

(54) METHOD FOR PRODUCING CATALYSTS CONTAINING RUTHENIUM AND THE USE THEREOF FOR HYDROGENATION

(75) Inventors: Stefan Antons, Leverkusen; Lutz Frohn, Erkrath; Jörg-Dietrich Jentsch, Krefeld, all of (DE); Andreas Schulze Tilling, League City, TX (US); Erich Wolters, Köln (DE)

(73) Assignee: Bayer Aktiengesellschaft, Leverkusen (DE)

(*) Notice: Subject to any disclaimer, the term of this patent is extended or adjusted under 35 U.S.C. 154(b) by 0 days.

(21) Appl. No.: 09/601,051
(22) PCT Filed: Jan. 16, 1999
(86) PCT No.: PCT/EP99/00236
§ 371 Date: Jul. 25, 2000
§ 102(e) Date: Jul. 25, 2000
(87) PCT Pub. No.: WO99/38613
PCT Pub. Date: Aug. 5, 1999

(30) Foreign Application Priority Data

Jan. 31, 1998 (DE) .......................................... 198 03 888

(51) Int. Cl.$^7$ ............................ B01J 31/00; B01J 21/08; B01J 21/18; C07D 305/12; C07C 27/00; C07C 27/04
(52) U.S. Cl. ...................... 502/104; 502/107; 502/185; 502/184; 502/243; 549/325; 549/326; 568/864; 568/885
(58) Field of Search ................................ 549/326, 325; 502/104, 185, 184, 243, 107; 568/864, 885

(56) References Cited

U.S. PATENT DOCUMENTS

| 4,214,106 A | * | 7/1980 | Freudenberger et al. | .... 568/864 |
| 5,149,680 A | * | 9/1992 | Kitson et al. | ................ 502/185 |
| 5,905,159 A | | 5/1999 | Fischer et al. | .............. 549/429 |

FOREIGN PATENT DOCUMENTS

| DE | 2132547 | 2/1973 |
| FR | 0 724 908 | 8/1996 |
| WO | 96/27436 | 9/1996 |

OTHER PUBLICATIONS

Houben–Weyl, Methoden der organischen Chemie [Method of Organic Chemistry], 4$^{th}$ edition, vol. VI/1b, pp. 103–107, (month unavailable) 1984, Primäre Alkohole aus Carbonsäuren bzw. Carbonsäureestern.

J. Org. Chem. 24, Dec. 1959, pp. 1847–1854, Broadbent et al, Rhenium and Its Compounds as Hydrogenation Catalysts. III. Rhenium Heptoxide$^{1,2,3}$.

* cited by examiner

Primary Examiner—Johann Richter
Assistant Examiner—Elvis O. Price
(74) Attorney, Agent, or Firm—Joseph C. Gil; Richard E.L. Henderson

(57) ABSTRACT

The invention relates to catalysts containing ruthenium and at least one other metal having an atomic number in the range of from 23 to 82 prepared by (a) mixing a suspension of a ruthenium compound having a specific surface area in the range of from 50 to 300 m$^2$/g with a solution of at least one metal compound in which at least one such metal compound contains a metal different from ruthenium and has an atomic number in the range of from 23 to 82, and (b) treating the mixture of the suspension and the solution with a reducing agent.

11 Claims, No Drawings

METHOD FOR PRODUCING CATALYSTS CONTAINING RUTHENIUM AND THE USE THEREOF FOR HYDROGENATION

This is the National Phase Application of PCT/EP99/00236, filed Jan. 16, 1999.

The present invention relates to a method for producing particularly advantageous catalysts which contain ruthenium and at least one other metal with an atomic number in the range from 23 to 82, and to the use, of such catalysts for hydrogenations.

It is known that carboxylic acids can be reduced catalytically with hydrogen to alcohols. A summarizing description thereof is given in Houben-Weyl, Methoden der organischen Chemie [Methods of Organic Chemistry], 4th edition, vol. VI/1b, pages 103–107 (1984). Where catalysts containing ruthenium are employed (see page 106), relatively high temperatures and very high pressures are necessary, for example temperatures of 145 to 190° C. and pressures of 700 to 950 bar.

J. Org. Chem. 24; 1847 (1959) describes a method for the hydrogenation of carboxylic acids in which rhenium oxide is employed as catalyst. However, long reaction times and high pressures are required. In addition, the yield and the selectivity are unsatisfactory.

Catalysts which, besides ruthenium, contain other metals, for example rhenium, are also known for various hydrogenations. Such multimetallic catalysts may be in Raney form, in sponge form or as supported catalysts. Thus, EP-A 724 908 describes Raney ruthenium catalysts which are modified by other metals and can be employed for various hydrogenations. However, they require large catalyst weights and long reaction times. The Raney ruthenium is prepared by leaching the aluminium out of a ruthenium/aluminium alloy with sodium hydroxide solution. This results in the Raney ruthenium catalyst containing residues of aluminium, and aluminium oxides and sodium hydroxide solution. This has adverse effects on the catalyst performance.

In addition, the handling of such catalysts is particularly complicated because they are pyrophoric.

DE-A 195 10 438 describes a method for producing 1,4-butanediol and tetrahydro-furan from furan, it being possible to employ as catalysts inter alia ruthenium/rhenium sponge. This can be obtained by reducing an aqueous $Re_2O_7/RuCl_3$ solution. Such catalysts have only unsatisfactory activities and selectivities.

WO 96/27436 describes catalysts containing ruthenium and rhenium which are applied to a support material consisting of carbon. The disadvantage of these catalysts is that for hydrogenations they require temperatures and pressures at which racemizations occur to a considerable extent on use of optically active precursors.

The preparation of ruthenium oxide of high purity with a high specific surface area is described in DE-A 2 132 547. This monometallic catalyst shows only low activities in the hydrogenation of carboxylic acids, however. In addition, if optically active precursors are employed, racemizations occur to a considerable extent.

A method for producing catalysts which contain ruthenium and at least one other metal with an atomic number in the range from 23 to 82 has now been found and is characterized in that a suspension of a ruthenium compound which has a specific surface area in the range from 50 to 300 $m^2/g$ is mixed with a solution of at least one metal compound where at least one of these metal compounds contains a metal different from ruthenium and having an atomic number in the range from 23 to 82, and the mixture of suspension and solution is treated with a reducing agent.

According to the present invention it is possible to produce, for example, bimetallic ruthenium/metal X catalysts and trimetallic ruthenium/metal X/metal Y catalysts. Catalysts produced according to the invention contain ruthenium and, for example, the metals X and, where appropriate, Y in elemental form and may be, for example, in the form of a colloid or in the form of intermetallic compounds. Examples of metals X and Y are rhenium, osmium, iron, cobalt, rhodium, palladium, platinum, copper, zinc, silver, tin, germanium, gallium, lead and tin. It is preferred according to the invention to produce catalysts which, besides ruthenium, contain one of the said metals or, besides ruthenium, contain combinations of rhenium with copper, silver or tin. Ruthenium/rhenium catalysts are particularly preferably produced.

The catalysts may contain the individual metal components in any ratios. Preferred catalysts are those in which the individual metals are present in equal atomic ratios, or ruthenium is present in excess. For ruthenium/metal X catalysts, for example, an Ru/X atomic ratio of 1/1 to 10/1, in particular of 1/1 to 5/1, is preferred.

A wide variety of suspending agents are suitable for preparing the suspension of a ruthenium compound. Water is preferred in this connection. Particularly suitable ruthenium compounds are those which can be reduced to the metal in a simple manner, for example with hydrogen. The ruthenium compounds may have various oxidation states, for example +3, +4 or +8. Ruthenium oxides and ruthenium oxide hydrates in which the ruthenium is present in the +4 oxidation state are preferred. Aqueous suspensions containing ruthenium oxide or ruthenium oxide hydrate of the necessary specific surface area are commercially available or can be produced in a known manner, for example by dissolving a water-soluble ruthenium compound, for example ruthenium trichloride, in water, making the solution alkaline and adding an oxidizing agent. A ruthenium (IV) oxide hydrate with a suitable specific surface area then precipitates. It is then possible by decantation, addition of water and acid and filtration to obtain an aqueous suspension of ruthenium (IV) oxide or oxide hydrate which can be employed directly for the catalyst production according to the invention.

Suitable suspensions of ruthenium compounds which have a specific surface area in the range from 50 to 300 $m^2/g$ and are suitable for the production according to the invention of catalysts are suspensions which contain, for example, 0.01 to 200% by weight of ruthenium, calculated as metal. These suspensions preferably contain 0.1 to 4% by weight of ruthenium. Preferred suspensions contain ruthenium compounds with a specific surface area in the range from 100 to 250 $m^2/g$.

The solution which contains at least one metal compound in which at least one metal different from ruthenium and having an atomic number in the range from 23 to 82 is present may contain as solvent for example those which are miscible with the suspending agent for the ruthenium compound. If the suspending agent for the ruthenium compound is, for example, water, the solvent for the other metal compound(s) may be, for example, water or $C_1$–$C_4$-alkyl alcohols. The suspending agent and the solvent is preferably water. Metal compounds which contain at least one metal different from ruthenium and having an atomic number in the range from 23 to 82 may be, for example, compounds, which are soluble in the particular solvent, of the metals which are indicated above as examples of metals X and Y. Aqueous solutions of rhenium compounds are preferably used, in particular aqueous solutions of rhenium heptoxide ($Re_2O_7$), which are also referred to as perrhenic acid ($HReO_4$ or $Re_2O_7 \times 2\,H_2O$).

The solution which contains at least one metal compound in which at least one metal different from ruthenium and having an atomic number in the range from 23 to 82 is present may contain, for example, 0.01 to 60% by weight of the metal compound(s), calculated as metal. This content is preferably 0.1 to 5% by weight.

It is also possible to proceed in such a way that the solution which contains at least one metal compound in which at least one metal different from ruthenium and having an atomic number in the range from 23 to 82 is present is generated in situ. For example, the metal compound(s) can be added in solid form to the suspension of a ruthenium compound with the necessary specific surface area and, where appropriate, additional solvent. Formation of the solution of the metal compound(s) and their mixing with the suspension of the ruthenium compound then take place simultaneously.

Treatment of the mixture of suspension and solution with a reducing agent can in principle be carried out with all reducing agents which are able to reduce the ruthenium compound and the other metal compound(s). It has proved advantageous in many cases, especially because virtually no interfering by-products are formed, to treat with hydrogen at temperatures in:the range from 50 to 200° C. and pressures in the range from 5 to 200 bar.

Since the catalysts produced according to the invention can preferably be employed for hydrogenations, the previously described reduction with hydrogen may also be carried out in the reaction vessel for the hydrogenation, preferably immediately before the hydrogenation itself.

It is also possible to proceed in such a way that a suspension of a ruthenium compound is reduced before the mixing with the solution of one or more compounds of other metals, and the suspension and the solution are reduced once again after the mixing.

Catalysts produced according to the invention show intimate contact of the metals present therein and specific surface areas of, for example, 50 to 150 $m^2/g$. The individual catalyst particles generally contain all the metals whose compounds were employed in the production of the catalyst. Virtually no particles which contain only one metal, for example only ruthenium, are present. This has emerged from microanalytical and electron microscopic investigations.

Catalysts produced according to the invention have high activity. This is surprisingly significantly higher than for catalysts of identical composition produced by reducing a solution containing a ruthenium compound and at least one metal compound of a metal different from ruthenium and having an atomic number in the range from 23 to 82 (see Example 5).

Catalysts produced according to the invention can be used in particular for hydrogenations. Important possible uses are, for example, the production of alcohols which are optically active where appropriate from carboxylic acids, carboxylic esters and carboxamides which are optically active where appropriate; the preparation of amino alcohols which are optically active where appropriate from amino acids, esters and amides which are optically active where appropriate, the preparation of alcohols from carboxylic acids, in particular of saturated diols from saturated or unsaturated dicarboxylic acids, dicarboxylic esters and dicarboxamides and the preparation of alcohols which are optically active where appropriate from hydroxy carboxylic acids, hydroxy carboxylic esters and hydroxy carboxamides which are optically active where appropriate. Individual examples are the preparation of L-1,2,4-butanetriol from L-malic acid, of L-alaninol from L-alanine, of n-butanol and 1,4-butanediol from maleic acid and of 1,6-hexanediol from adipic acid. Hydrogenations with catalysts produced according to the invention can be carried out, for example, at 0 to 120° C. and 5 to 300 bar.

Catalysts produced according to the invention can be modified, where appropriate by treatment with sulphur compounds, for example thioethers.

Catalysts produced according to the invention are free of support materials, aluminium, aluminium oxides and alkalis.

Catalysts produced according to the invention are distinguished by the possibility of carrying out with them hydrogenations under milder conditions, in higher yields, with substantial retention of optical activities and/or with negligible impairment of functional groups otherwise present. In addition, not particularly large amounts of catalyst are required, and the reaction times are generally distinctly shorter than with ruthenium-containing catalysts of the state of the art.

The present invention also relates to ruthenium-containing catalysts which are free of support materials and which are obtainable by mixing a suspension of a ruthenium compound which has a specific surface area in the range from 50 to 300 $m^2/g$ with a solution of at least one metal compound where at least one of these metal compounds contains a metal different from ruthenium and having an atomic number in the range from 23 to 82, and the mixture of suspension and solution being treated with a reducing agent.

EXAMPLES

Example 1 a) Preparation of a Ruthenium Oxide Hydrate Suspension 103 g of ruthenium trichloride were dissolved in 7.75 l of water and heated to 50° C. While stirring at 50° C., a 20% by weight aqueous sodium hydroxide solution was added dropwise until a pH of 8 was reached. Then, while stirring, 1.125 l of a 2% by weight aqueous hydrogen peroxide solution were added, and the mixture was stirred at 50° C. for 30 min. The precipitated product was allowed to settle, one decantation was carried out, the volume was made up to 10 l with water, and another decantation was carried out. The mixture was then made up to 3.3 l and stirred at 80° C. for 6 hours, and 4.5 ml of acetic acid were added. After cooling, the precipitate present was filtered off. 412 g of ruthenium oxide hydrate were obtained in the form of a pasty slurry with a ruthenium content of 12% by weight. The specific surface area of the precipitate was determined after drying in vacuo at 100° C. by the BET method to be 210 $m^2/g$.

b) Addition of Rhenium and Reduction 99.3 g of ruthenium oxide hydrate water-moist (obtained as in a)) and 6.3 g of rhenium heptoxide (containing 76.9% by weight of rhenium) were introduced into a 0.7 l stainless steel autoclave. It was flushed twice with nitrogen and twice with hydrogen, 100 bar of hydrogen were injected and, while stirring (800 rpm), the mixture was heated to 120° C. After this temperature was reached, the hydrogen pressure was increased to 150 bar and the catalyst was reduced at 120° C. for 1 hour. The autoclave was subsequently decompressed and the catalyst was filtered off. Neither ruthenium nor rhenium were detectable in the filtrate. The dried catalyst contained less than 1% by weight of sodium and less than 1% by weight of chlorine. The average size of the ruthenium/rhenium particles was determined by laser light scattering to be 16 $\mu$m The specific surface area of the catalyst was determined after drying in vacuo at 100° C. by the BET method to be 70 m²/g.

Example 2

The procedure was as in Example 1 but the temperature was maintained at 60° C. during the reduction. Once again, the filtrate contained neither ruthenium nor rhenium.

Example 3

The procedure was as in Example 1 but the reduction was carried out under a hydrogen pressure of 10 bar. The filtrate contained no ruthenium but contained rhenium in an amount of 200 mg/l, which is equivalent to 3.5% by weight of the rhenium employed.

Example 4

The procedure was as in Example 1 but 240 mg of iron in the form of iron oxalate were added instead of the rhenium heptoxide.

Example 5

(For comparison—no deposition of ruthenium oxide hydrate)

9.83 g of ruthenium trichloride and 6.3 g of rhenium heptoxide (containing 76.9% by weight of rhenium)n were introduced in 100 ml of water into a 0.7 l stainless steel autoclave. It was flushed twice with nitrogen and twice with hydrogen, 100 bar of hydrogen were injected and, while stirring (800 rpm), the autoclave was heated to 120° C. After this temperature was reached, the hydrogen pressure was increased to 150 bar and the catalyst was reduced at 120° C. for 1 hour. The autoclave was subsequently decompressed and the catalyst was filtered off. The filtrate contained 0.074 mg/l ruthenium and 0.39 mg/l rhenium.

Example 6

Hydrogenation of L-malic acid using the catalyst obtained as in Example 1.

The catalyst obtained in Example 1 was placed in a 0.7 l stainless steel autoclave, the volume was made up with 100 ml of water and the mixture was heated to 60° C. This was followed by flushing twice with nitrogen and twice with hydrogen, and 278 g of an 18.9% by weight aqueous solution of L-malic acid were aspirated in. The mixture was then stirred (800 rpm) at 60° C. under a pressure of 200 bar of hydrogen until hydrogen uptake ceased. After cooling to room temperature, the catalyst was filtered off, the product solution was neutralized with sodium hydroxide solution, and the water was distilled out of the resulting crude solution. 42.0 g of a colourless viscous liquid remained and were distilled under a pressure of 1 mbar. After a fore-run which consisted of butanediols, 33.9 g of 97.9% by weight of L-1,2,4-butanetriol were obtained (boiling point 133° C./1mbar; ee=98.8%). This corresponds to a yield of 79.8% based on malic acid employed.

Examples 7 to 10

The procedure was as in Example 6 but the catalysts obtained in Examples 2, 3, 4 and 5 were employed. The results obtained are evident from Table 1.

TABLE 1

|  | Catalyst after | Yield | ee |
| --- | --- | --- | --- |
| Example 7 | Example 2 | 78.9% | 98.8% |
| Example 8 | Example 3 | 84.8% | 97.8% |
| Example 9 | Example 4 | 62.9% | 94.3% |
| Example 10 | Example 5 | 6.6% | not determined (comparative example) |

Examples 11 to 14
(Comparative examples—of rhenium-free catalyst)

A catalyst was prepared as in Example 5, But no rhenium heptoxide was employed. This catalyst was employed for the hydrogenation of L-malic acid in analogy to Example 6 at various temperatures. The results obtained are evident from Table 2.

TABLE 2

|  | Temperature | Yield*) | ee |
| --- | --- | --- | --- |
| Example 11 | 60° C. | no conversion | — |
| Example 12 | 80° C. | 19.9% | 90.9% |
| Example 13 | 100° C. | 68.2% | 78.4% |
| Example 14 | 120° C. | 45.2% | 0.1% |

*)of L-1,2,4-butanetriol

Example 15
Hydrogenation of L-alanine

A suspension of 6 g of ruthenium/rhenium catalyst obtained as in Example 1 was introduced together with 100 ml of water into a 0.7 l stainless steel autoclave. To this was added a solution of 60.0 g of L-alanine and 32.9 g of sulphuric acid in 370 g of water. After flushing with nitrogen, 100 bar of hydrogen were injected. The temperature was raised to 60° C. and the hydrogen pressure was increased to 200 bar over a course of 30 min. After a reaction time of 7 h, hydrogen uptake had ceased. The reaction mixture was cooled to room temperature and decompressed, and the catalyst was removed by filtration, and the water was distilled out of the filtrate. The residue remaining after the distillation out of the water was adjusted to a pH of 11.4 with 59.7 g of 45% by weight aqueous sodium hydroxide solution and was fractionally distilled under 50 mbar. 35.7 g of pure L-alaninol were obtained (boiling point: 94° C./50 mbar); ee>than 99.9%. This corresponds to a yield of 71% of theory. The ee was determined by gas chromatography.

Example 16
(Comparative example—of rhenium-free catalyst)

A catalyst was produced as in Example 1 but without adding rhenium. L-alanine was reduced with this catalyst as described in Example 15. The hydrogenation time was increased in this case to 35 h. The yield and the ee of the resulting L-alaninol corresponded to Example 15.

Example 17
(Hydrogenation of maleic acid)

9.6 g of the water-containing catalyst obtained as in Example 1 were introduced in 200 ml of water into a 0.7 l stainless steel autoclave. To this was added a solution of 52.5 g of maleic acid in 125 ml of water. After flushing with nitrogen, 100 bar of hydrogen were injected. The temperature was raised to 100° C. and the hydrogen pressure was raised to 200 bar. After a reaction time of 3.7 h, the hydrogen uptake had ceased. The reaction mixture was cooled to room temperature and decompressed, and the catalyst was removed by filtration. The filtrate was investigated by gas chromatography, and the proportions of reaction products evident from Table 3—ignoring water—were found.

TABLE 3

| Component | Content (GC %) |
|---|---|
| Tetrahydrofuran | 4% |
| n-Propanol | 1% |
| n-Butanol | 22% |
| 1,4-Butanediol | 64% |
| Unknown substances | 8% |

Example 18

Hydrogenation of Adipic Acid a) Catalyst activation 14 g of ruthenium oxide hydrate water-moist (containing 7.61% by weight of ruthenium) and 1.4 g of rhenium heptoxide (containing 76.9% by weight of rhenium) were introduced into 280 g of water in a 0.7 l stainless steel autoclave. The autoclave was flushed twice with nitrogen and twice with hydrogen and heated to 120° C. while stirring (800 rpm). After this temperature was reached, the hydrogen pressure was raised to 150 bar and the catalyst was reduced at 120° C. for 1 hour.

b) Hydrogenation of Adipic Acid

The autoclave was cooled and decompressed, and 70 g of adipic acid were added. It was then flushed with nitrogen and hydrogen and, at 100° C. and 200 bar, hydrogen was injected for 8 h. The reaction mixture was then cooled to room temperature and decompressed, and the catalyst was removed by filtration. The filtrate was investigated by gas chromatography. This showed the proportions of reaction products—ignoring water—presented in Table 4.

TABLE 4

| Component | Content (GC %) |
|---|---|
| n-Pentanol | 1.2% |
| n-Hexanol | 7.12% |
| 1,6-Hexanediol | 85.0% |
| 6-Hydroxycaproic acid | 6.6% |
| Adipic acid | 0% |

What is claimed is:

1. A method for producing catalysts containing ruthenium and at least one other metal having an atomic number in the range of from 23 to 82 comprising
    (a) mixing a suspension of a ruthenium compound having a specific surface area in the range of from 50 to 300 $m^2/g$ with a solution of at least one metal compound in which at least ode such metal compound contains a metal different from ruthenium and has an atomic number in the range of from 23 to 82, and
    (b) treating the mixture of the suspension and the solution with a reducing agent.

2. A method according to claim 1 wherein the catalyst produced is a bimetallic ruthenium/metal X catalyst or a trimetallic ruthenium/metal x/metal Y catalyst, wherein X and Y independently denote rhenium, osmium, iron, cobalt, rhodium, palladium, platinum, copper, zinc, silver, tin, germanium, gallium, lead, or tin.

3. A method according to claim 1 wherein the catalyst produced is a ruthenium/rhenium catalyst.

4. A method according to claim 1 wherein the suspension of the ruthenium compound contains 0.01 to 20% by weight of ruthenium, calculated as the metal.

5. A method according to claim 1 wherein the solution containing a metal compound other than a ruthenium compound contains a total of 0.01 to 60% by weight of one or more such metal compounds, calculated as the metal.

6. A method according to claim 1 wherein the treatment with a reducing agent is carried out using hydrogen at a temperature in the range of from 50 to 200° C. and a pressure in the range of from 5 to 200 bar.

7. A ruthenium-containing catalyst that is free of support materials obtained by a method comprising
    (a) mixing a suspension of a ruthenium compound having a specific surface area in the range of from 50 to 300 $m^2/g$ with a solution of at least one metal compound in which at least one such metal compound contains a metal different from ruthenium having an atomic number in the range of from 23 to 82, and
    (b) treating the mixture of the suspension and the solution with a reducing agent.

8. A process comprising hydrogenating in the presence of a catalyst according to claim 7.

9. A process according to claim 8 comprising hydrogenating a saturated or unsaturated dicarboxylic acid, dicarboxylic ester, and/or dicarboxamide to form a diol.

10. A process according to claim 8 comprising hydrogenating an amino acid, ester, and/or amide to form amino alcohol.

11. A process according to claim 8 comprising hydrogenating a hydroxy carboxylic acid, hydroxy carboxylic ester, and/or hydroxy carboxamide to form an alcohol.

* * * * *